United States Patent [19]

Kahil et al.

[11] Patent Number: 4,492,115

[45] Date of Patent: Jan. 8, 1985

[54] METHOD AND APPARATUS FOR MEASURING DEFECTS IN FERROMAGNETIC TUBING

[75] Inventors: John E. Kahil; Mark S. Jaynes; James E. Bradfield, all of Houston, Tex.

[73] Assignee: PA Incorporated, Houston, Tex.

[21] Appl. No.: 599,162

[22] Filed: Apr. 11, 1984

[51] Int. Cl.³ .................. G01N 27/82; G01N 27/72
[52] U.S. Cl. .................. 73/151; 324/226; 324/229; 324/232
[58] Field of Search .......... 73/151; 324/221, 226, 324/232, 237, 238, 229

[56] References Cited

U.S. PATENT DOCUMENTS

| | | | |
|---|---|---|---|
| 913,780 | 12/1962 | Whitehead . | |
| 3,103,976 | 9/1963 | de Vries et al. | 166/46 |
| 3,237,446 | 3/1966 | Wood | 324/226 |
| 3,343,079 | 9/1967 | Crouch | 324/37 |
| 3,379,970 | 4/1968 | Kusenberger et al. | 324/37 |
| 3,401,332 | 9/1968 | McClurg et al. | 324/232 |
| 3,529,236 | 9/1970 | Proctor | 324/37 |
| 3,538,433 | 11/1970 | Wood et al. | 324/37 |
| 3,555,412 | 1/1971 | Fowler | 324/37 |
| 3,579,099 | 5/1971 | Kanbayashi | 324/37 |
| 3,612,987 | 10/1971 | Placke et al. . | |
| 3,693,075 | 9/1972 | Forster | 324/229 |
| 3,843,923 | 10/1974 | de Vries | 324/34 R |
| 3,916,301 | 10/1975 | Vild et al. | 324/37 |
| 3,940,689 | 2/1976 | Johnson, Jr. | 324/37 |
| 4,247,819 | 1/1981 | Shimanda et al. | 324/233 |
| 4,292,589 | 10/1981 | Bonner | 324/221 |

*Primary Examiner*—Howard A. Birmiel
*Attorney, Agent, or Firm*—Norvell & Associates

[57] ABSTRACT

A method and apparatus for determining the extent of defects in ferromagnetic tubular elements comprising a continuous string for use in an oil or gas well is disclosed. The tubing trip tool measures tubing average wall thickness, local defects, such as corrosion pitting, and axial defects, such as sucker rod wear during removal of the tubing from the well. Tubing velocity is also measured, and couplings between tubing sections are detected and counted, in order to specify the axial location of defects on each tube, and also provide a profile of the condition of the overall string. A saturating magnetic field and a fluctuating magnetic field are applied to the tubing and the magnitude of the induced fields and the changes are measured to quantify defects in the tubing.

13 Claims, 18 Drawing Figures

METHOD AND APPARATUS FOR MEASURING DEFECTS IN FERROMAGNETIC TUBING

BACKGROUND OF THE INVENTION

1. Field of the Invention

This invention relates to defect inspection of tubular elements comprising a generally continuous tubular string used in a subterranean oil and gas well.

2. Description of the Prior Art

Continuous tubular strings formed of connectable tubular sections or elements, such as production tubing strings, strings of drill pipe and casing strings, are used in the drilling, completion and production of subterranean oil and gas wells. The tubular elements comprising such strings are subject to mechanical damage while the tubular elements are located within the well and are also subject to the action of corrosive fluids which may be contained within the tubular elements or which may be transported through the tubular string between the well surface and a downhole location. It is therefore advantageous that the individual tubular elements comprising a tubular string be inspected periodically. Commonly, tubular elements or tubular sections are inspected for defects after the tubing string is removed from the well. Conventional inspection of tubular sections normally occurs after the individual tubing sections comprising the tubing string have been disengaged. Defect inspections are conventionally performed on a section by section basis.

A number of techniques exist for determining the presence of a defect in a tubing section. For example, the precise location of internal and external radially extending and three dimensional defects, including slug inclusions, mechanical damage, corrosion pitting and fatigue cracks, has been determined by flux leakage techniques in which a longitudinal magnetic field is induced by one or more magnetic induction coils. Surface riding detectors are located around the tubing and the maximum signal is recorded to precisely locate the defect.

A common way of detecting longitudinal defects magnetically is the "rotating pole" method, where the magnetic field is applied from the outside by rotating electromagnets, and detectors positioned in-between the poles scan the outside surface of the pipe. Tubing wall thickness has been measured by measuring the radiation from an external rotating radioactive source of gamma radiation transmitted through the wall of a tubing section to a detector positioned inside the pipe. Other ways of measuring wall thickness with gamma radiation, which are backscatter, double-wall through-transmission and chord, have both the radiation detector and the source located on the outside of the pipe.

Techniques requiring surface-riding detectors, insertion of a detector or a driving means within the bore of tubular elements or requiring rotating mechanical means to obtain a complete circumferential coverage of tubing sections are unsuited for use in defect inspection and measurement of tubing sections while the string is being removed from the well. These defect inspection techniques are also unsuited to the measurement of defects in tubing sections while the sections are interconnected in the tubing string. Thus these inspection techniques are not suitable for use on a drilling, completion or workover rig at the surface of the well to measure defects in a tubing string as the string is removed from the well.

One technique for inspecting tubular elements which is adaptable to relative movement, at variable velocities, is a technique involving the use of a saturating longitudinal magnetic field and the subsequent measurement of the time integral of the electrical signal caused by the magnetic field applied to the ferromagnetic tubular member to determine the average wall thickness. Testing using this technique has been conducted for surface pipe installations in which the magnetic field and the flux detecting elements are moved relative to a continuous pipe array. Such apparatus has not, however, been employed to measure the average wall thickness of tubing sections as they are removed from an oil or gas well.

SUMMARY OF THE INVENTION

The method and apparatus disclosed herein is used to determine the extent of defects in ferromagnetic tubular elements comprising a continuous string used in an oil or gas well. The tubing trip tool measures tubing average wall thickness; local defects, such as corrosion pitting; and axial defects, such as wear due to sucker rod interference, during removal of the tubing from the well.

A uniform magnetic property is induced in at least a portion of the tubing. In the preferred embodiment, an appropriate longitudinal magnetic field is induced by applying an appropriate uniform magnetizing field. The magnitude of the electric signal integral from this field determines the tubing wall thickness.

Flux leakage in the longitudinal magnetic field is related to the presence of local defects, such as corrosion pitting. The shape of the flux leakage field is determined, for example by geometric signal processing, to quantify the depth of the local defects. In the preferred embodiment, multiple flux leakage detecting elements, such as Hall effect probes, are used to determine two different derivatives of the flux leakage, and the depth of the local defects, such as corrosion pits, in a function of both different derivatives evaluated at their local maximums.

The presence of axial defects, having an axial dimension in excess of the local defects is determined by applying a fluctuating magnetic field in addition to the first uniform magnetic field. Driven fields induced in the tubing element by the fluctuating field are then used to measure the axial defects. In the preferred embodiment the fluctuating fields are generated by two coils having sinusoidal conductor distributions of different phases around the tubing. The driven fields are also detected by using two sinusoidal detector coils having sinusoidal conductor distributions of different phases. The applied fluctuating field is rotated around the tubing using stationary coils and the presence of axially extending defects at various angular positions can be detected.

DESCRIPTION OF THE PREFERRED EMBODIMENTS

TUBING TRIP TOOL

Figure 1:
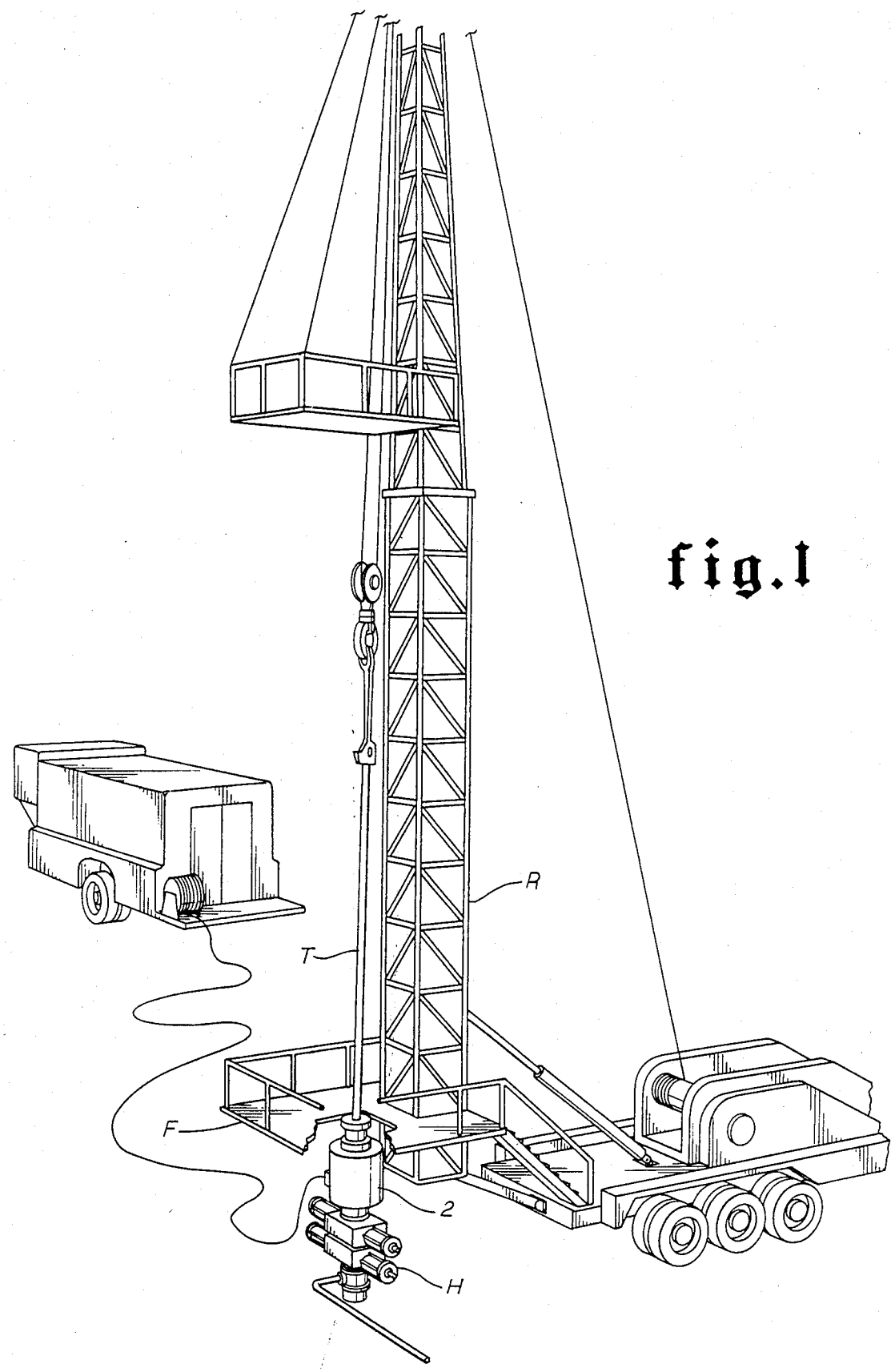
FIG. 1 is a schematic of the tubing trip tool on a surface rig.

A conventional workover rig illustrated schematically by rig R in FIG. 1, is used to remove a tubular string, such as a casing, drilling or tubing string represented by tubing string T, from an oil or gas well during workover operations. Workover operations normally involve the removal of the tubular string to permit operations intended to restore or increase production in a producing wall. Typically the original tubing string is reused if the respective tubular elements are in satisfactory condition. FIG. 1 illustrates the use of a tubing trip tool 2 at the rig site to measure defects in each tubular element as it is removed from the well. A tubing trip tool 2 comprising the preferred embodiment of this invention can be positioned on the wellhead H below the rig floor F so as not to interfere with conventional operations on the rig. The tubing trip tool can be attached directly to the blow out preventers on the well.

Figure 2:
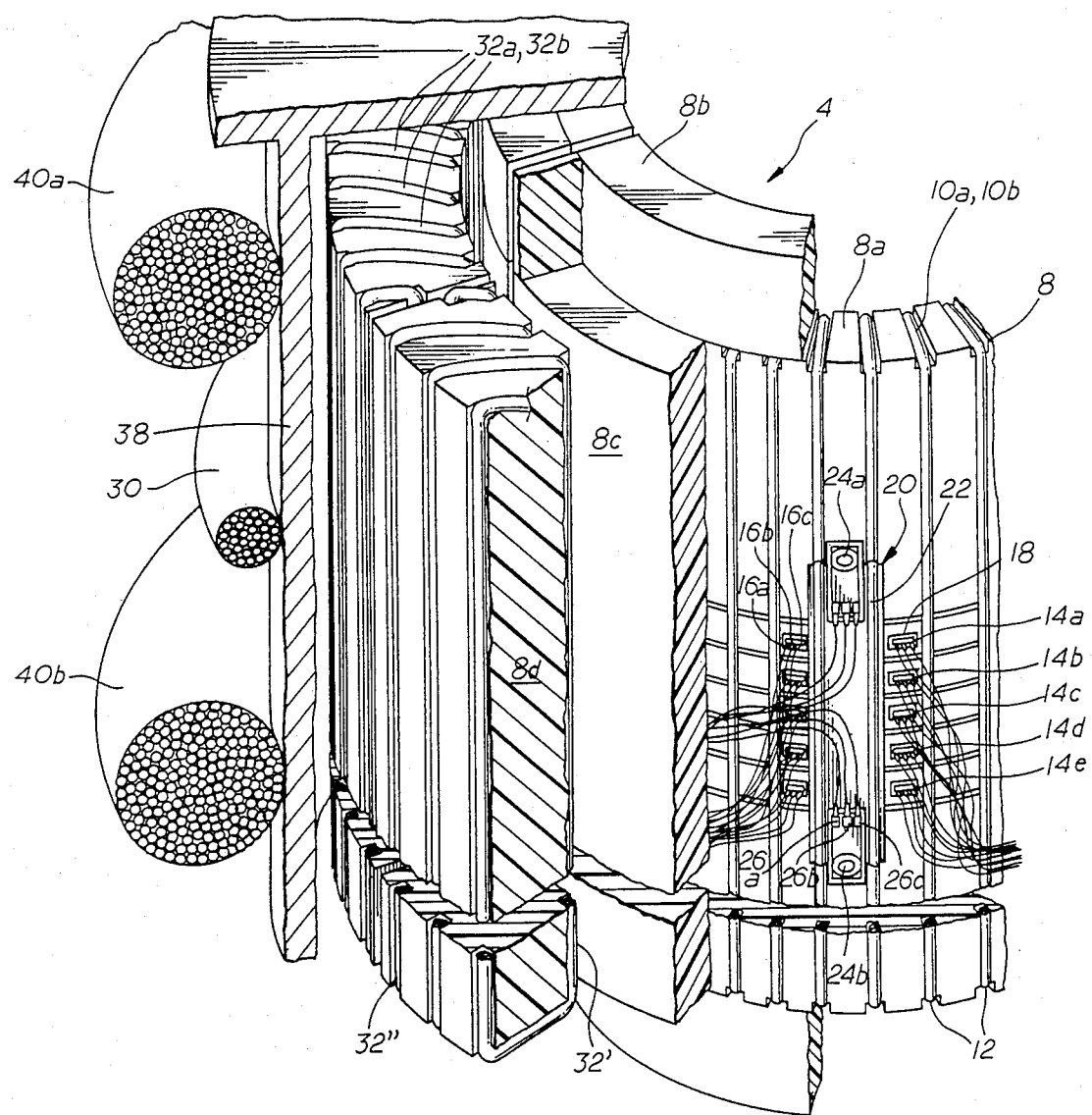
FIG. 2 is a view of a segment of the tubing trip tool in the expanded configuration.
Figure 3:
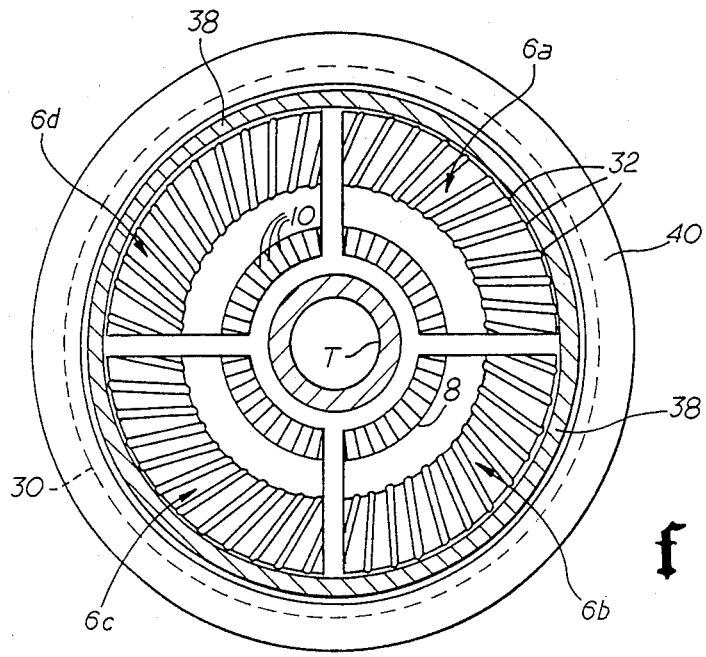
FIG. 3 is a cross-sectional view of the tubing trip tool head in the expanded configuration.

A segment of the tubing trip tool head 4 is shown in FIG. 2. The head includes two separate driving coils, two separate detecting coils, and a plurality of discrete detecting elements to determine the extent of defects in the tubing sections. A velocity detector for determining relative velocity between the head and tubing sections is also included. The preferred embodiment of this invention comprises an expandable head having four segments 6a-6d as seen in FIG. 3. Each segment is an encasement 8 which comprises multiple components. The encasement 8 is fabricated from a material that has the properties of an electrical insulator. In the preferred embodiment of this invention, encasement 8 can be formed from an encapsulation material or potting compound which will insure that the proper amount of space is maintained between the electrical components. The encapsulation material will occupy any spaces or voids surrounding the components, and will provide a barrier between the electrical components and the atmosphere surrounding encasement 8, thereby rendering encasement 8 safe for use on the wellhead where explosive vapors can be encountered.

Two separate AC detecting coils 10a and 10b are carried on the innermost insulating body section 8a. The circumferentially continuous coils 10a and 10b are wound in appropriate grooves on body section 8a and a plurality of separate loops are formed around body 8a. These separate loops, each of which contains conductors forming the separate detecting coils 10a and 10b, are positioned in a radial plane on encapsulating member 8a. Each loop is generally defined by two radially spaced, axially extending coil conductor sections and two axially spaced, radially extending coil conductor sections. The coil conductors then define an annular volume encircling the tubular sections passing axially therethrough. Radially extending planes between the coil conductors will be generally perpendicular to magnetic field lines detected by coils 10a and 10b as will be subsequently more completely discussed.

A plurality of flux leakage detecting elements 14a-14e are also located in the inner encapsulating body section 8a. In the preferred embodiment of this invention, each of the flux leakage detecting probes 14a-14e comprises a separate probe in which voltage is generated in response to the Hall effect. The plane of each Hall probe is perpendicular to the axis of the tubing trip tool head 4 and is located perpendicular to each tubular element moving axially relative to the tubing trip tool head 4. In the preferred embodiment of this invention, separate groupings of five Hall effect flux leakage detecting probes are positioned at different angular positions around the tubing trip tool head 4. Each of the Hall probes 14a-14e is received within corresponding slots 18 extending into the insulating body section 8a. In the preferred embodiment of this invention, five equally spaced probes are positioned at each angular location.

One or more velocity detectors 20 is positioned on the exterior of insulating body section 8a. In the preferred embodiment of this invention, each velocity detector 20 comprises a detector circuit or coil 22 having two or more Hall probes 24a and 24b located within the circuit. The plane of the velocity detector circuit or coil 22 is perpendicular to a radial plane extending through the tubing trip tool head 8. The plane of the individual Hall probes 24a and 24b in the velocity detector is perpendicular to the plane of the Hall probe 14a-14e used for flux leakage detection.

The AC magnetic detecting coils 10a and 10b, the flux leakage detecting probes 14a-14e and the velocity detector 20 are each radially spaced from the tubing element T in which defects are to be measured. In the segmented embodiment of the invention shown in FIG. 2, the individual segments can be shifted radially from a measuring position to an outer position to permit obstructions to move past the tubing trip tool head. Each of the detector coils is, however, spaced from the surface of the tubing T in the inner measuring position. In the preferred embodiment of this invention, the inner surface of the tubing trip tool head 4 is positioned approximately two-thirds of an inch from the surface of the tubing element T. Insulated body sections 8b and 8c surround the detecting coils and probes mounted on insulating body section 8a. Epoxy or some other potting material can also be used to insure that all potential electrical leakage paths are appropriately isolated from each other and from the atmosphere.

Outer AC driving coils 32a and 32b are positioned around insulating body section 8d. The AC drive coils 32a and 32b each comprise continuous coils having an angular conductor distribution similar to that of AC detecting coils 10a and 10b. The sinusoidal distribution in the coils 32a and 32b is relatively offset so that the conductor distribution phase differs between drive coils 32a and 32b. In the preferred embodiment of this invention, the conductor distribution is offset by 90° so that coil 32a can be referred to as a sine coil and coil 32b can be referred to as a cosine coil. Coils 32a and 32b each completely encircle the tubing trip tool head 4 and tubular element T with separate loops, containing conductors from each coil 32a and 32b, being formed in radial planes around the tubing trip tool head 4. On the exterior, AC driving coils 32 are encapsulated within the common encapsulating insulating body 8 of the tubing trip tool 2.

In the preferred embodiment of this invention, an outer metal sheath 38 can be positioned around the exterior tubing trip tool head. This outer metal sheath, which can be fabricated from a nonferromagnetic material, such as aluminum, serves as a carrier for the outer DC drive coils 40a and 40b and for encircling coil 30. In the preferred embodiment of this invention, the DC drive coils are separated into two separate bundles. A single drive coil bundle can also be used. The encircling drive coils 40 contain a sufficient number of amp turns to saturate the tubular element T passing through the tubing trip tool. Encircling coil 30 extends completely around the circumference of the tubing trip tool head 4 and surrounds the tubular element T at a greater radial spacing than the detecting elements 10a and 10b, 14a-14e, and 20.

WALL THICKNESS MEASUREMENT

The tubing trip tool 2 measures the wall thickness of a tubing section by using a technique in which the total flux induced in the tubing section by a saturating magnetic field is measured. The ferromagnetic tubing section within the saturating magnetic field is saturated when the magnitude of the magnetic field induced in the ferromagnetic element is at a maximum and does not increase as a result of a further increase in the saturating magnetizing field. Thus the saturating magnetizing field can produce a uniform saturated magnetic field in a tubing section having a specified cross-sectional area. In other words, the total magnetic flux is dependent upon the cross-sectional area or wall thickness of the tubular section. If the saturating magnetizing field is uniform, the contribution of the total flux induced by the magnetization of the pipe material within a given area varies as the cross-sectional area of the tubing section. By providing a large number of amp turns in a coil 40 encircling a tubing section, a saturated magnetic field extending longitudinally within the wall of the tubing section can be produced.

The total flux through an area intersecting the axis of the tubing section and intersecting the longitudinal saturated magnetic field can be measured by pickup coil 30 encircling the tubular section. The area of the pickup coil would preferably, but not necessarily, be perpendicular to the axis of the tubing section. The total flux through the pickup coil can be detected by signal integration. The EMF induced in a pickup coil is directly related to the time rate of change of the flux through the coil. Thus the total flux can be detected by integrating the EMF produced in the coil over time. In fact, a virtually linear dependence of the total flux through the pickup coil with average wall thickness can be obtained. Thus a convenient direct measurement of average wall thickness can be made.

LOCAL DEFECT DETECTION

The average wall thickness of a ferromagnetic tubular member or pipe can be determined by detecting the total flux induced by the saturating magnetizing field within the element. Qualitative information as to the changes in surface texture due to such factors as internal and external corrosion, can be determined by comparing average wall thickness at different locations on the tubular member. The difference between the signals produced in separate coils will not yield quantitative information as to the state of local defects in the tubular members.

In tubular sections used in oil and gas wells, corrosion on the tubular member can result in localized corrosion pits $D_1$ which can seriously reduce the strength of individual tubing sections. Since the thickness of the remaining wall of the tubular sections determines the ability of individual tubular sections to function in the work environment, the depth of local corrosion pits must be quantified to determine the acceptability of the tubular sections.

It is common practice to grade used tubing based upon the depth of corrosion pits. Although each separate corrosion pit would constitute a local defect $D_1$, the dimensions of which would generally be less than the diameter of the tubular element, the nature of the corrosion phenomenon would result in a plurality of irregular and overlapping corrosion pits being located in the same general region on the interior of a tubular section. Of course the flux leakage will be dependent upon the overall size of individual corrosion pits and not just the depth of the corrosion pits. Thus the length and width of the corrosion pits would affect the flux leakage detected. Other factors, such as the contour or shape of the corrosion pits and the extent of any discontinuities in the shape of corrosion pits, would also affect the flux leakage. Thus the leakage fields of different pits having the same depth in a tubular section will differ for different lengths and widths of the pits as well as for a different contour of the pits. Background fields or noise due to unrelated phenomenon can also affect the signal corresponding to flux leakage and the saturated magnetic field within the pipe.

In the preferred embodiment of this invention, a plurality of flux leakage detecting elements 14 are disposed within the saturating magnetizing field. These flux leakage detecting elements are disposed at a plurality of axially spaced positions within the saturating magnetizing field. In the preferred embodiment of this invention, a plurality of discrete probes having an output produced by the Hall effect are used. In the preferred embodiment of this invention, identical flux leakage detecting Hall probes 14a-14e are equally spaced at five separate axial positions. Although only two sets of flux leakage detecting Hall probes 14a-14e are shown in FIG. 2, it should be understood that corresponding sets of multiple elements are circumferentially disposed around the tubing trip tool head to provide complete coverage around the periphery of the tubular element to detect local defects, such as corrosion pits located at different angular positions.

In the preferred embodiment of this invention, the individual flux leakage detecting Hall probes are oriented such that the plane of the Hall sensing element is perpendicular to the axis of the moving tubular element. Hall elements, such as the type used herein, produce an output voltage proportional to the product of the input current, the magnetic flux density, and the sine of the angle between the magnetic flux density and the plane of the Hall generator. Thus a maximum voltage output from a given leakage field would be produced by orienting the individual flux leakage detecting Hall probes perpendicular to the saturated magnetic field. The DC drive coils 40a and 40b are positioned to induce a longitudinal or axial saturated magnetic field within the tubular element T. By orienting the probes 14a–14e perpendicular to the longitudinal saturated magnetic field within the pipe, the flux leakage detecting probes are saturated to detect longitudinal changes in the magnetic field.

It has been found that the magnitude of the flux leakage detected by elements 14 does not provide an adequate quantitative measure of the depth of local defects, such as corrosion pitting defects, on a tubular element. The fact that flux leakage is dependent upon the size and shape of localized defects, such as corrosion pitting, rather than upon the depth alone, is believed to account for the inability to measure localized defect depth by measuring flux leakage magnitude alone. However, it has been found if effects due to the length and width of defects, such as corrosion pitting, can be removed, the resulting signal results in an accurate measurement of the depth of the local defect.

In the preferred embodiment of this invention, a signal corresponding to the depth of local defects, such as defects due to corrosion pitting, can be determined by differentiation of the magnitude of the flux leakage relative to the axial or longitudinal dimension of the moving tubular member. A signal corresponding to the depth of local defects, such as defects due to corrosion pitting, can be obtained by comparing two derivatives of different orders, each with respect to the axial dimension of the flux leakage, obtained when the saturated magnetic field is at the maximum value of the flux leakage corresponding to each measured discontinuity. In the preferred embodiment of this invention, the second and fourth derivatives, determined by using finite element approximations, can be combined to produce a signal measuring the depth of the local defect. It has been found that the depth of a local defect can be measured in the following fashion.

$$d = k \frac{(f'')^a}{(f'''')^b};$$

where d is equal to the depth of local defects, such as a defect due to corrosion pitting.

k is an empirically determined proportionality constant.

f'' is the second derivative of the flux leakage with respect to the axial or longitudinal dimension.

f'''' is the fourth derivative of the flux leakage with respect to the axial dimension.

a is an empirically determined factor.

b is an empirically determined factor.

Figure 4:
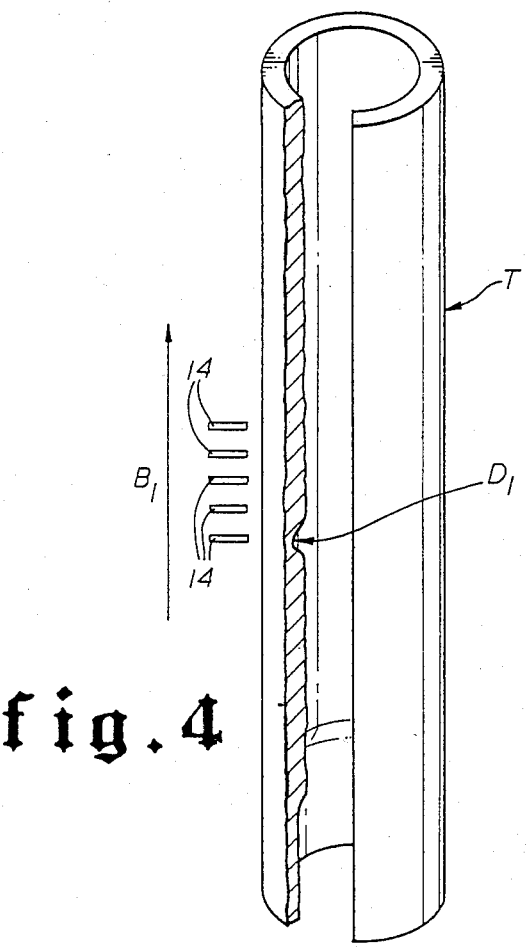
FIG. 4 is a view of the tubing string and the detectors for measuring local defects.
Figure 5:
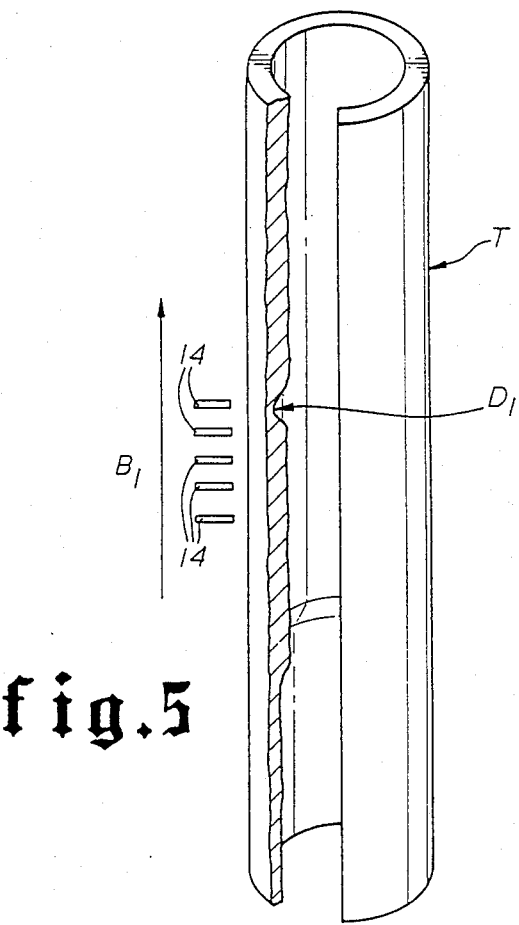
FIG. 5 is a view similar to FIG. 4 showing relative movement of the tubing.
Figure 6:
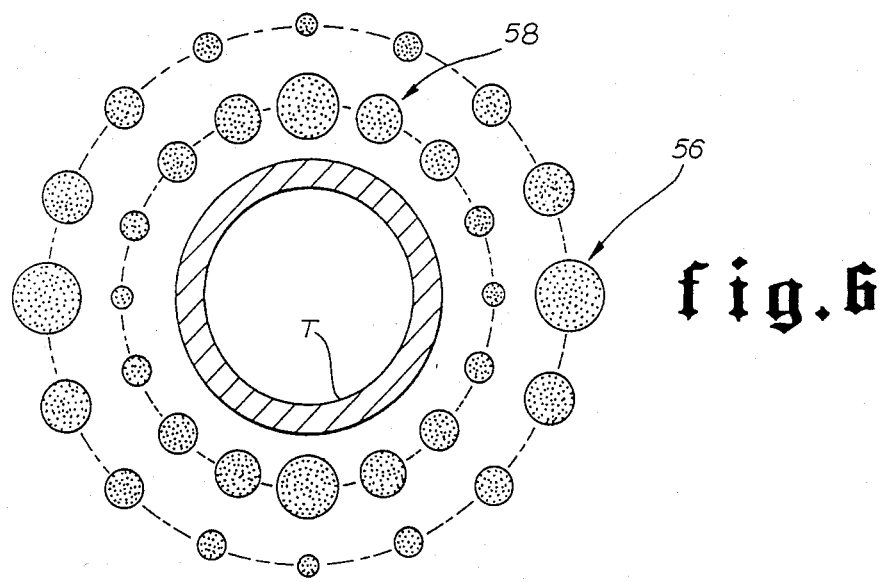
FIG. 6 is a cross-sectional schematic showing the sinusoidal distribution of sine and cosine windings relative to the tubular element.

In the preferred embodiment of this invention, the geometric filtering or numerical differentiation is obtained by using a plurality of axially evenly spaced flux leakage detecting elements 14a–14e which remain fixed relative to each other (See FIGS. 4 and 5). By multiplying the magnitude of the flux leakage simultaneously detected in each element by appropriate factors and summing, the value of each of the higher order derivatives can be determined. In the preferred embodiment of this invention, the factors used to multiply the output of individual flux leakage detecting elements are constants and are chosen such that the value of each of the derivatives will be zero if the flux leakage is unchanging. The conventional voltage generating flux leakage detection elements 14a–14e employed in the preferred embodiment of this invention are spaced apart and a simultaneous value of flux leakage is obtained from each flux leakage detecting element 14.

AXIAL DEFECT MEASUREMENT

The bore of a tubular member or tubing section T used in a tubular string in a subterranean oil and gas well can often have axially extending defects $D_2$ located at one or more circumferential positions on the tubing. An example of axially extending defects are defects due to sucker rod wear. Sucker rod wear on the bore of the tubing occurs when the sucker rod contacts the tubing during reciprocal movement of the sucker rod. However, sucker rod interference is not uniform around the circumference of the bore of the tubing section or tubular element. Sucker rod wear often occurs at only one circumferential location, although it is not uncommon for a sucker rod to oscillate laterally causing sucker rod interference at two opposite points. The loads placed on the individual sucker rod assembly will normally result in continual interference between the sucker rod and the tubing at the same locations.

Axial defects $D_2$, such as defects due to sucker rod interference, can be detected by employing a fluctuating AC magnetizing field $B_2$ in addition to a uniform DC magnetizing field $B_1$. Even if a uniform DC magnetizing field in the longitudinal or axial direction is of sufficient intensity to saturate the ferromagnetic element or tubular section within the DC field, as is the case with the field used to determine wall thickness, the addition of a fluctuating AC transverse magnetic field will result in detectable changes in the magnetic state of the ferromagnetic element located within both fields. In fact, the DC field enhances the penetration of the AC field in the tubular sections. Of course the detectable changes resulting from the addition of the fluctuating transverse field will be dependent upon the geometry of the tubular element. For example, the response of an undamaged tubing section would differ from the response of a similar tubing section containing an axially extending defect, such as a rod wear interference defect. In the preferred embodiment of this invention, the changes due to such axially extending defects as sucker rod interference defects $D_2$ in an oil field tubular section can be detected even where the strength of the fluctuating transverse magnetic field is significantly less than the strength of a uniform saturating DC magnetizing field. It has been found that measurement of axial defects, such as sucker rod interference defects, can be made by applying a sinusoidal transverse magnetizing field having a frequency of approximately 100 Hz. and an intensity of approximately 1/10th the intensity of a uniform saturating magnetizing field applied in the longitudinal direction. In the preferred embodiment of this invention, drive coils 32 are used to apply such a fluctuating magnetizing field.

Figure 8:
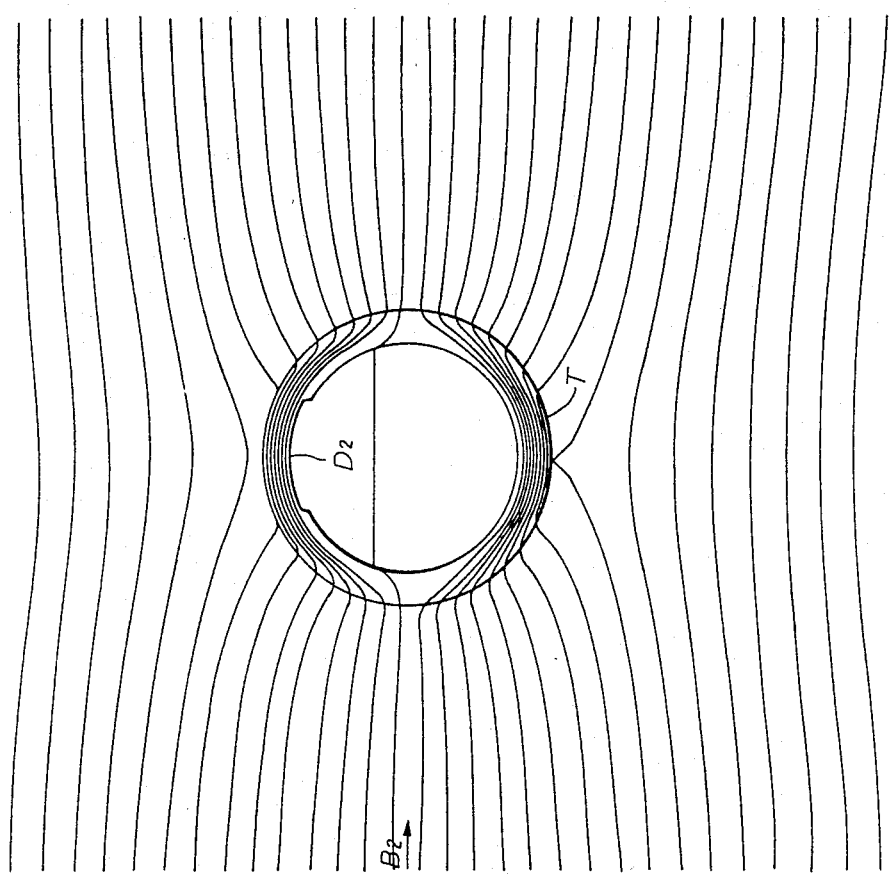
FIG. 8 is a view similar to FIG. 7 showing the total fluctuating magnetic field lines as effected by an annular section of a tubular element containing an axially extending defect on the internal surface of the tubular element.
Figure 7:
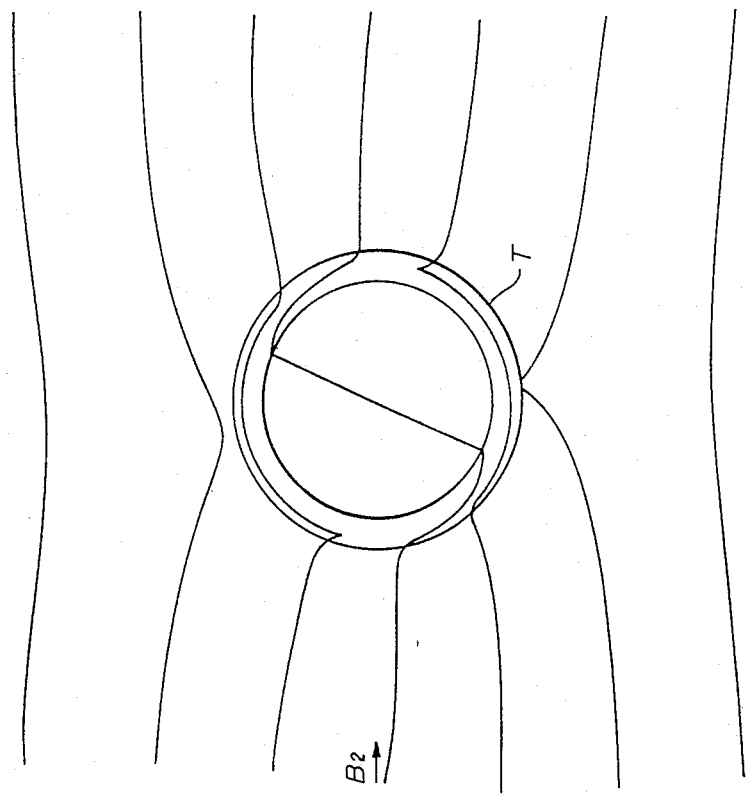
FIG. 7 shows the total fluctuating magnetic field lines as disturbed by the annular cross-section of a tubular element having no axially extending defects.
Figure 9:
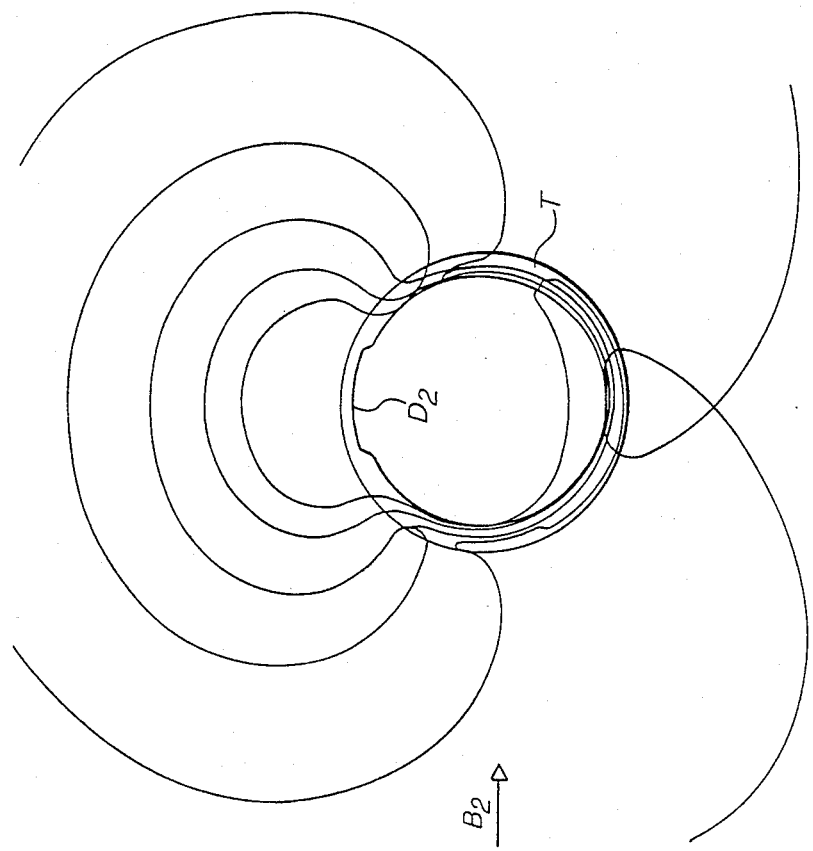
FIG. 9 is a view showing the difference in field lines between the magnetic fields shown in FIGS. 7 and 8.
Figure 12:
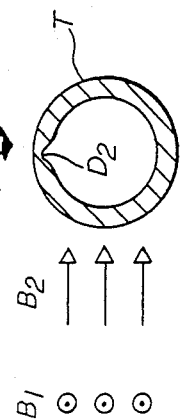
FIGS. 12-15 illustrate the rotation of the fluctuating magnetic field around a tubular element to detect axially extending defects at different angular positions relative to the driving magnetic field.
Figure 13:
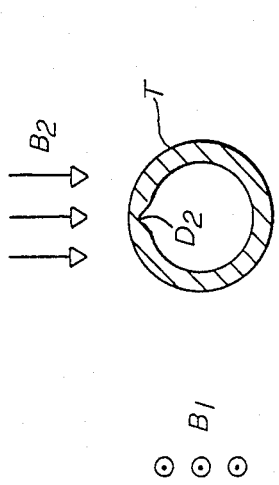
Figure 14:

Although the response due to the application of a transverse fluctuating magnetic field in addition to the uniform longitudinal saturating magnetic field will in part be due to flux leakage effects, the principal response will be due to eddy current effects. Eddy current effects will occur in both ferromagnetic and nonferromagnetic tubular members. The field changes resulting from the imposition of the fluctuating AC field are depicted in FIGS. 7-9. In FIGS. 7-9, the magnetic field lines in a plane perpendicular to the axis of a tubular section are shown as they are affected by undamaged and damaged annular sections of tubing T.

In order to obtain full circumferential coverage of a tubular section and to obtain a measurable response, the preferred embodiment of this invention comprises an apparatus and method for rotating the fluctuating AC magnetizing field around the tubular section T as the tubing section moves axially relative to both the AC magnetizing field $B_2$ and the uniform DC saturating magnetizing field $B_1$. Thus the rod wear defect response measured in the preferred embodiment of this invention is due to an AC magnetizing field rotating around the tubing section and having a constant magnitude.

The rod wear detecting apparatus employed in tubing trip tool head 4 in the preferred embodiment of this invention can detect and measure rod wear defects $D_2$ at arbitrary circumferential positions in a tubing section or tubular element which may be moving axially at different and nonuniform velocities. When used in a tool for detecting rod wear defects as a tubing string is removed from an oil and gas well, the velocity of the tubing sections can be up to 300 feet per minute. Rotation of the magnetic field around the moving tubular sections to obtain complete circumferential coverage of the tubing sections cannot be practically accomplished by mechanically rotating the apparatus inducing the transverse fluctuating magnetizing field. In the preferred embodiment of this invention, rotation of the magnetic field is accomplished by employing separate phase windings in the drive coils 32 which generate the fluctuating transverse field. Thus the field is rotated electrically rather than mechanically. In the preferred embodiment of this invention, the drive coils 32a and 32b each have a conductor distribution which varies sinusoidally with the angular orientation around the drive coils. The conductor distributions in the two sinusoidal coils 32a and 32b are angularly displaced such that the phase of the conductor distribution in coil 32a differs from that in coil 32b. The sinusoidal drive coil as used in the preferred embodiment of this invention has a phase displacement equal to 90° so that coil 32a may be referred to as a sine coil and coil 32b may be referred to as a cosine coil. The space or angular displacement of the conductor distribution between the two phase windings and the time displacement of the current are such that a rotating field of constant angular speed and constant amplitude is generated. FIGS. 12-15 illustrate the rotation of the constant AC magnetic field $B_2$ in the presence of the constant DC magnetic field $B_1$ as the AC magnetic field rotates around the tubing section T containing an axial defect $D_2$.

Figure 10:
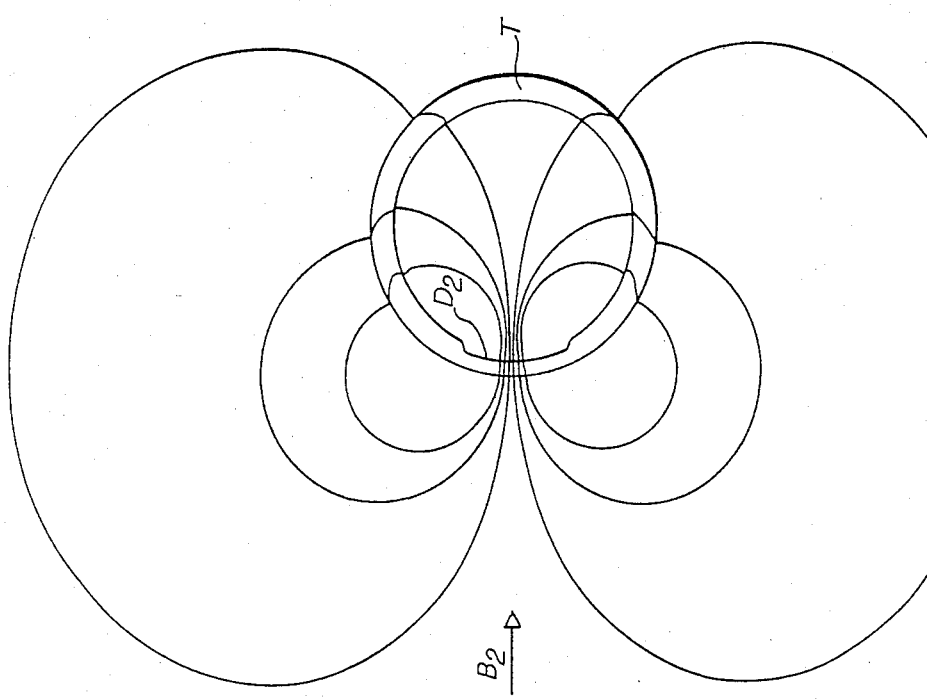
FIGS. 10 and 11 are views similar to FIG. 9 showing the differential field lines for different orientations of an axially extending defect relative to the driving magnetic fields.
Figure 11:
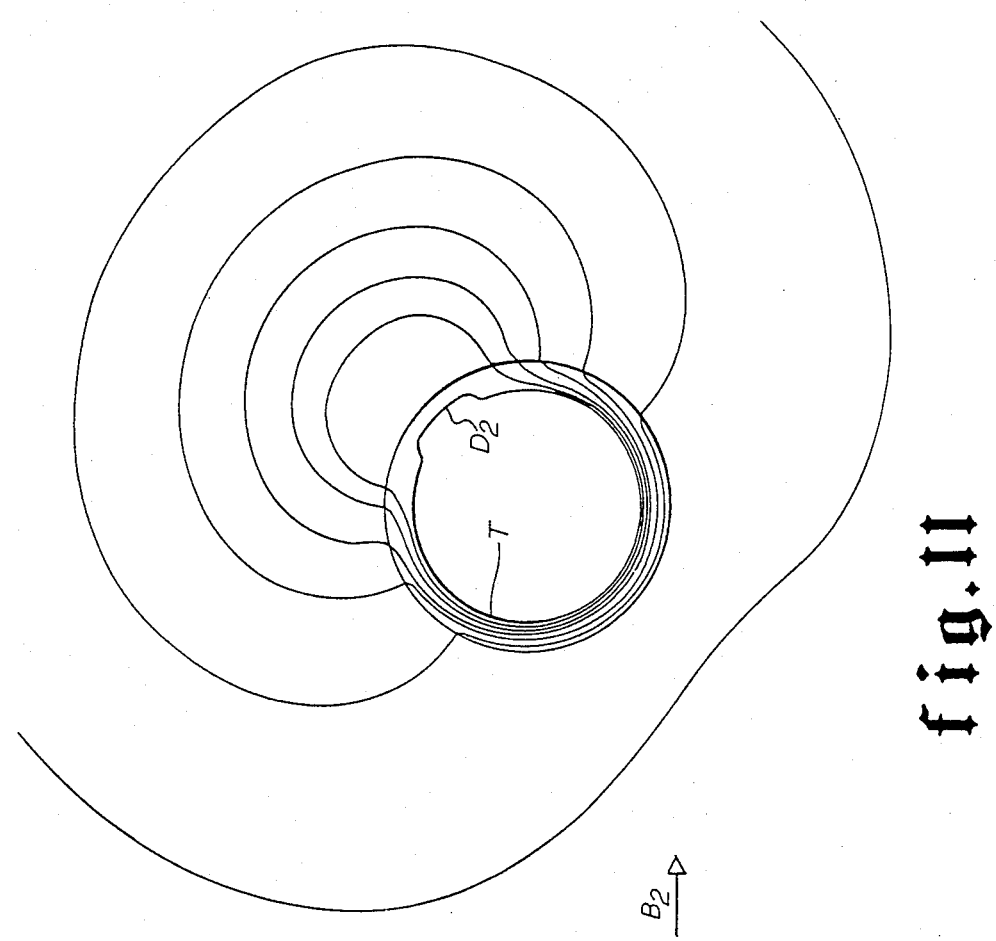
Figure 15:
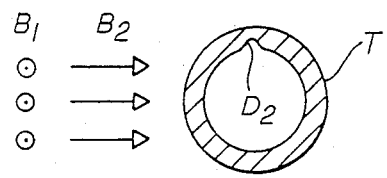

It is apparent in FIGS. 9-11 that the disturbed or differential magnetic field lines due to axial defects $D_2$ as they appear in planes perpendicular to the moving tubing element T, are primarily circular. In the preferred embodiment of this invention, these differential field lines are detected by AC detecting coils 10a and 10b which are distributed around the circumference of the tubing trip tool head 4. The plane of each individual coil 10 is oriented generally transversely with respect to the circular field lines generated by axially extending defects, such as the circular field lines in FIGS. 9-11. Thus the changing magnetic flux linking each coil will be detected by coils 10a and 10b.

The detector or pickup coil 10 comprises a pair of vertical coils 10a and 10b. In the preferred embodiment of this invention, each of the detector coils 10a and 10b has a sinusoidal distribution of detecting coil conductors. The conductor distribution of one sinusoidal coil is displaced relative to the other sinusoidal coil so that there is a phase displacement between conductor distributions. In the preferred embodiment of this invention, this phase displacement is equal to 90° so that one detector coil 10a can be referred to as the sine detector coil while the other detector coil 10b can be referred to as the cosine detector coil. Of course the circular driven field lines, as represented in FIGS. 9-11, would differ in intensity at different angular positions depending upon the location of the axial defect $D_2$ relative to the driving magnetic field produced by coils 32a and 32b. If the defect occurred in the vicinity of a portion of the cosine coil having a large distribution of conductors, the signal generated in the cosine coil would be significantly larger than the signal generated in the sine coil, because the sine coil would have a correspondingly smaller electrical conductor distribution in the vicinity of the axial defect. Since the distribution of conductors at different positions in the two coils is known, appropriate gain factors can be used to adjust the combination of signals in the two separate detector coils 10a and 10b, so that the resultant signal reflects both the size and location of the axial defect.

The two detecting coils 10a and 10b comprise sinusoidal coil windings similar in construction to the drive coil 32 shown in FIG. 2. Since the coils 10 extend completely around the circumference of tubular element T, a defect at any circumferential location will generate signals in both of the sinusoidal detecting coils 10a and 10b. Since the conductor distribution, and hence current, in each of the coils varies angularly around the tubular element T, the disturbed or differential field will produce a different signal in the coils at different angular positions.

The eddy current and flux leakage effects sensed by the detector coils 10a and 10b are manifested by amplitude changes and by phase changes. For example, the phase of the eddy current is 90° out of phase with the field generated by the driving coils 32. Clearly then eddy current effects will result in a phase change of the detected signal with respect to the driving signal. In the preferred embodiment of this invention, this change in phase is detected to measure the size of axially or longitudinally occurring defects, such as defects due to rod wear interference, which have a length generally greater than the diameter of the tubular element 2.

Combined analog and digital signal processing can be employed to obtain the magnitude of signals produced in both the sine detecting coil 10a and the cosine detecting coil 10b. However, in order to determine if the signals produced in both coils are due to a defect in a tubular element or are due to some other disturbance, such as uniform wall loss, some means of determining the angular variation of the signals must be employed.

The signals in the detecting coils 10a and 10b can be detected and processed by analog and digital signal processing to obtain the magnitude of signals produced in both the sine detecting coil 10a and the cosine detecting coil 10b. The drive coils 32a and 32b are each driven at the same frequency. These drive coils are driven at a frequency of 100 Hz in the preferred embodiment of this invention. The detector coils 10a and 10b are also positioned around the tubular element T and the signals in coils 10a and 10b are split up into a number of separate channels. Appropriate gain factors related to the angular variation of the windings in the detector coil are chosen to separate the signals from detector coils 10a and 10b into discrete signals in separate channels. In the preferred embodiment of this invention, the windings are sinusoidal and are displaced by 90°. The signal in each channel is therefore obtained by multiplying the signal in each coil by appropriate sinusoidal functions and then combining to obtain the signal in each separate channel. In the preferred embodiment of this invention, the voltage in each channel is obtained according to the following formula:

$$V_{channel} = V_s \text{ Sin Angle} + V_c \text{ Cos Angle};$$

where $V_s$ is equal to the voltage obtained in one of the detector coils 10a which can be referred to as the sine coil and $V_c$ is equal to the voltage in coil 10b which can be referred to as the cosine coil. By using a gain factor related to the winding distribution in the detector coils and by summing the product of the appropriate gain factor with the voltage in the coil in question, a resultant channel signal will be obtained which can be compared with signals in the other channels to obtain signals corresponding to angular positions around the tubular element T.

VELOCITY AND POSITION DETECTOR

Figure 16:
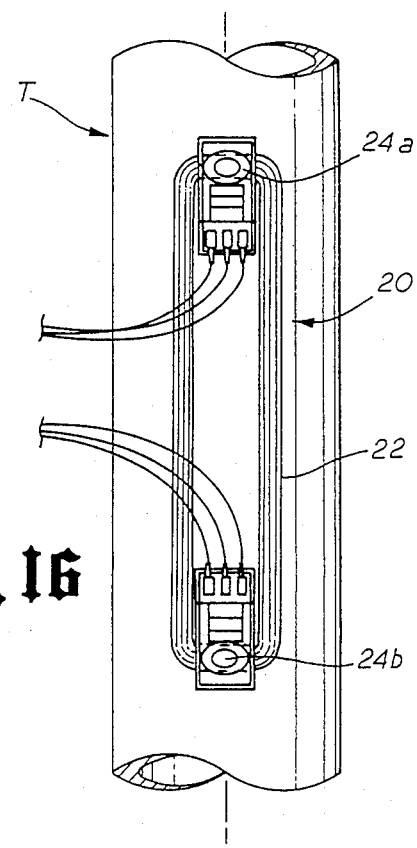
FIG. 16 is a view of a velocity detector mountable on the tubing trip tool head.

The cross-sectional area of a moving tubular element, the depth of local defects, such as corrosion pitting defects, and the size of longitudinally extending defects, such as defects due to sucker rod interference, can be determined by detector 4 independent of the velocity of the tubular element T relative to the detector. There may also be a need to determine the velocity of the tubular element T relative to the tubing trip tool 2. For example, it may be necessary to not only determine the existence and size of a defect in a particular tubing section of tubular string T, but it may be necessary to determine the position of the defect in both the tubing string and in the constituent tubular section. A noncontact velocity detector 20 is shown positioned on the tubing trip tool head 4 in FIG. 2. The preferred embodiment of each velocity detector used in this invention comprises two detector elements 24a and 24b in which a signal is produced by the magnetic field. In the preferred embodiment of this invention, detector elements 24a and 24b comprise elements in which the voltage is generated due to the Hall effect. These Hall probes 24a and 24b are then incorporated into a velocity detector coil 22 as shown schematically in FIG. 16. The signal produced in the coil is related to both the velocity and the magnetic field sensed by the coil. The signal in the coil is proportional to the vector cross product of the velocity and the magnetic field whereas the signals in the Hall probes are due solely to the magnetic field. The output voltage of a pickup coil near a changing magnetic field is proportional to the rate of change of the field of fixed spatial orientation passing by the coil, then any output voltage is proportional to the product of the field strength and the field velocity.

The changing magnetic fields due to the velocity of the tubular element T are the magnetic leakage fields emanating from the pipe either as pitting signals, as signals due to average wall changes, or as pipe noise. For example, a leakage field is created by permeability fluctuations within the ferromagnetic tubular element T. In the preferred embodiment of each velocity detector, the two Hall probes 24a and 24b are incorporated into the coil 22 with the Hall probes oriented to detect radial changes in the leakage fields. When the coil and Hall probes are oriented as shown in FIG. 2, the coil voltage is equal to the product of the number of turns in the coil, the velocity of the tubular element, the width of the coil, and the difference between the radial components of the magnetic leakage field at the two ends of the coil. The voltage of each Hall probe is equal to the gain of the Hall probe device times the radial component of the leakage field of the Hall probe. The ratio of the coil voltage to the difference in the voltage between the two Hall probes thus determines the pipe velocity.

END COUPLING DETECTOR

The noncontact velocity detector described herein can be used to determine the axial position of a defect in an inspected tubular member. Knowledge of the defect location in specific tubular sections forming the tubing string is important, and knowledge of the defect location in the tubing string is also significant in that such knowledge would permit the operator to determine the exact location in the well at which wall thickness reduction, corrosion pitting or wear due to sucker rod interference is a problem. Such knowledge would permit construction of a string profile to determine significant problem areas.

In order to construct a string profile and to accurately obtain information as to the location of defects in any particular tubular string, the position of the tubing string relative to the well head must be determined. In the preferred embodiment of this invention, the location of the tubing string is determined by use of the noncontact velocity detector and by use of a noncontact end coupling detector. For conventional tubular strings, such as casing, production tubing and completion strings used in oil and gas wells, the individual sections are joined by end couplings having a larger cross-sectional area.

Figure 17:
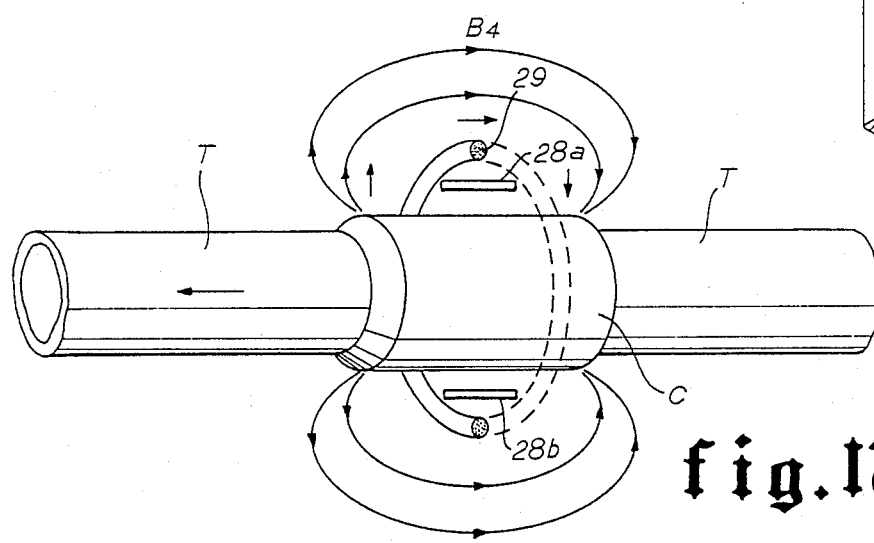
FIG. 17 is a view of the end coupling detector.
Figure 18:
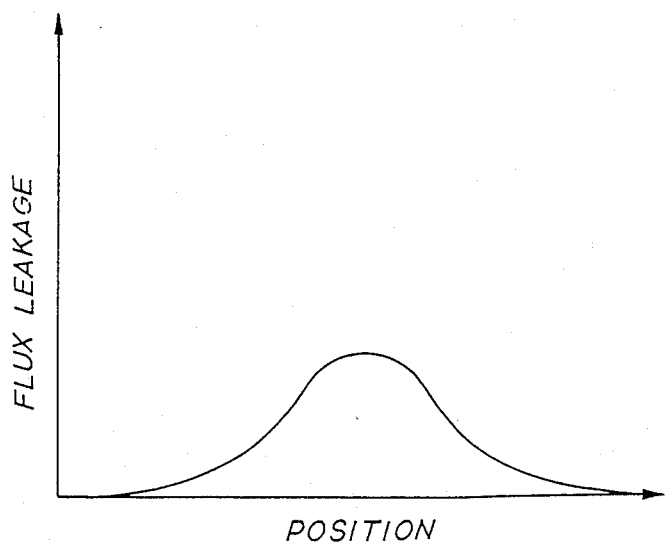
FIG. 18 shows the effect of movement of the tubular element upon flux leakage.

The exact location of each tubing section, and thus the location within the tubular string can be determined by detecting both the presence and the direction of movement of each end coupling. In the preferred embodiment of this invention, a magnetic field having a uniform strength and fixed relative to the well head is applied to the portion of the tubular string and tubular sections in the vicinity of the well head. An induced magnetic field in the tubular section results. FIG. 17 shows tubing sections T interconnected by end coupling C and the lines of magnetic flux representing the induced magnetic field B4 in the area of end coupling C. Since the cross-sectional area at end coupling C is greater than the cross-sectional area of tubing T, the strength of the magnetic field B4 in the vicinity of the end coupling will be greater than the strength of the magnetic field induced in the tubular section intermediate its ends. If the strength of the magnetic field B4 detected at the well head is greater than a predetermined reference value in excess of the field strength normally induced in a tubing section having a constant cross-sectional area intermediate its ends, the presence of a coupling can be distinguished from normal variations in the strength of the induced magnetic field in the tubing section. In the preferred embodiment of this invention, the strength of the reference signal or the threshold value of the magnitude of the induced magnetic field would be less than the magnitude of a magnetic field normally induced by an end coupling of known dimensions to account for slight variations of the magnetic field induced in the coupling.

Once the presence of the end coupling has been detected by encircling coil 29, the direction of movement can be detected by separate detectors, such as detectors 28a and 28b. In the preferred embodiment of this invention, detectors 28a and 28b comprise Hall probes which generate a voltage proportional to the product of the input current, the magnetic flux density, and the sine of the angle between the magnetic flux density and the plane of the Hall generator. These elements are similar to the elements used for corrosion pitting detection and the voltage is produced in response to the electromagnetic phenomenon generally referred to as the Hall effect. The sign of the output voltage of Hall probes 28a and 28b will be opposite when subjected to magnetic lines of force in a magnetic field extending in opposite directions. As shown in FIG. 17, in which the direction of movement of the tubular string T is in the direction of the arrow, the magnetic lines of force of magnetic field B4 extend in the directions shown. Magnetic lines of force for the end coupling C increase in intensity as the end coupling C moves into an applied magnetic field when the magnetic lines of force extend outward as shown. At the trailing edge of the end coupling C, the magnetic lines of force in the induced magnetic field B4 extend inwardly toward the tubular string T and end coupling C as shown schematically in FIG. 17. Thus the Hall probes 28a and 28b will be subjected to magnetic lines of force or flux extending in opposite directions during passage of end coupling C through the applied magnetic field. When the Hall probes 28a and 28b are positioned near the leading edge of the moving end coupling C, the magnetic lines of force will extend radially outward. When the Hall probes 28a and 28b are adjacent the trailing edge of the end coupling C, they will be subjected to magnetic line of forces extending inwardly toward end coupling C. Thus the voltage generated by Hall probes 28a and 28b in the vicinity of the leading edge of end coupling C will have the opposite sign from the voltage generated when the Hall probes 28a and 28b are in the vicinity of the trailing edge of end coupling C. One sequence of the signs of the voltage generated by Hall probes 28a and 28b will correspond to movement of the tubing string T and end coupling C in one direction. Movement of the tubing string T and the end coupling C in the opposite direction will result in an opposite sequence for the signs of the voltage generated by the Hall probes 28a and 28b. Thus the direction of movement of end coupling C through the applied magnetic field can be recognized by conventional computing means and specific tubular sections can be located.

When used in conjunction with a position indicator, such as would be provided by a device capable of measuring the velocity of the tubing string T, a profile of defects, including average wall thickness reduction, corrosion pitting, and wear due to sucker rod interference, can be tabulated as a function of the position of the tubular string in the well. Such information can give the operator valuable insights on the phenomenon being encountered within a subterranean oil or gas well. Furthermore, the use of the end coupling detector and the velocity detector described in the preferred embodiment of this invention will permit an accurate tabulation of defects in individual used tubing sections, to permit the operator to determine if such tubing sections should be replaced.

Although the invention has been described in terms of the specified embodiment which is set forth in detail, it should be understood that this is by illustration only and that the invention is not necessarily limited thereto, since alternative embodiments and operating techniques will become apparent to those skilled in the art in view of the disclosure. Accordingly, modifications are contemplated which can be made without departing from the spirit of the described invention.

What is claimed and desired to be secured by Letters Patent is:

1. Apparatus for simultaneously determining the extent of defects in used tubular elements forming a tubular string after use in a subterranean oil or gas well comprising:
   first means for determining the extent of the reduction in average wall thickness of each tubular element;
   second means for determining the extent of corrosion pitting in each tubular element;
   third means for determining the extent of wear due to sucker rod interference on each tubular element, the first, second and third means being mutually compatible wherein the reduction in wall thickness, the extent of corrosion pitting and the wear due to sucker rod interference can be simultaneously determined at the same location on a tubular element; and
   means for positioning the apparatus in a fixed position at the surface of a well whereby defects in the tubular elements can be detected by multiple, overlapping, compatible inspection means as the tubular elements travel relative to the apparatus into or out of the well.

2. The apparatus of claim 1 wherein said first, second and third means each comprise magnetic means.

3. The apparatus of claim 1 wherein the second means comprises magnetic means for detecting the flux leakage in a magnetic field induced in the tubular elements.

4. The apparatus of claim 1 wherein the third means comprises means for inducing a cyclic magnetic field in the tubular elements and means for detecting the fields induced in each tubular element by the cyclic magnetic field.

5. The apparatus of claim 4 wherein the means for inducing the cyclic magnetic field comprises electrical conductors sinusoidally distributed around the tubular elements for producing a magnetic field rotating around each tubular element.

6. The apparatus of claim 5 wherein the means for detecting the fields induced in each tubular member comprises electrical conductors sinusoidally distributed around the tubular elements.

7. The apparatus of claim 1 further comprising means for detecting the velocity of each tubular element simultaneously with the detection of defects therein.

8. The apparatus of claim 1 further comprising means for detecting the passage of end couplings on contiguous tubular elements moving past the apparatus.

9. The apparatus of claim 1 comprising a first drive coil disposable surrounding each tubular element, the first means comprising first detector coil means disposable surrounding each tubular element for detecting the total magnetic flux in each tubular section in response to the magnetic field induced therein by electric current in the first drive coil.

10. The apparatus of claim 9 wherein the second means comprises a plurality of detecting elements for detecting flux leakage in magnetic fields induced in each tubular element by the electric current in the first drive coil.

11. The apparatus of claim 10 wherein the detecting elements comprise elements responsive to the Hall effect.

12. The apparatus of claim 1 wherein the means for positioning the apparatus comprises means for mounting the apparatus on blow out preventers located at the surface of a subterranean well.

13. A method of determining the extent of defects in used tubular elements forming a tubular string after use in a subterranean oil or gas well, comprising the steps of:

determining the extent of the reduction in average wall thickness at successive positions on each tubular element at the well surface during movement of each tubular element into or out of the well;

determining the extent of corrosion pitting at successive positions on each tubular element at the well surface during movement of each tubular element into or out of the well;

determining the extent of wear due to sucker rod interference at successive positions on each tubular element at the well surface during movement, into or out of the well, wherein the determination of the reduction in wall thickness, corrosion pitting, and wear due to sucker rod interference are simultaneously determined at the same position on each tubular element.

* * * * *